United States Patent [19]

Yoon

[11] Patent Number: 5,171,250

[45] Date of Patent: Dec. 15, 1992

[54] SURGICAL CLIPS AND SURGICAL CLIP APPLICATOR AND CUTTING AND TRANSECTION DEVICE

[76] Inventor: InBae Yoon, 2101 Highland Ridge Dr., Phoenix, Md. 21131

[21] Appl. No.: 515,641

[22] Filed: Apr. 2, 1990

Related U.S. Application Data

[63] Continuation of Ser. No. 49,526, May 14, 1987, abandoned.

[51] Int. Cl.$^5$ .................. A61B 17/12; A61B 17/32
[52] U.S. Cl. ............................ 606/142; 606/170
[58] Field of Search ............. 606/120, 174, 142, 143, 606/170

[56] References Cited

U.S. PATENT DOCUMENTS

| 2,316,297 | 4/1943 | Southerland et al. | 128/326 |
| 3,006,344 | 10/1961 | Vogelfanger | 128/318 |
| 3,608,544 | 9/1971 | Schnepper | 128/326 X |
| 3,827,277 | 8/1974 | Weston | 128/326 X |
| 3,954,108 | 5/1976 | Davis | 128/325 |
| 3,989,049 | 11/1976 | Yoon | 128/326 |
| 4,428,374 | 1/1984 | Auburn | 606/174 |
| 4,440,170 | 4/1984 | Golden et al. | 128/325 |
| 4,682,598 | 7/1987 | Beraha | 128/305 |
| 4,759,364 | 7/1988 | Boebel | 606/142 |

FOREIGN PATENT DOCUMENTS 0095249 11/1983 European Pat. Off. ............ 128/346

Primary Examiner—Michael H. Thaler

[57] ABSTRACT

Single or double U-shaped surgical clips having leg faces with mating projections and apertures for securely locking tissue therebetween. An applicator device for applying the clips have walls temporarily receiving the clips, the walls having grooved surfaces to receive clip legs. The applicator has a sliding blade structure for severing tissue or for taking a transection. The applicator has a multiple handle assembly for effecting movement of slidably interfitting members, to accomplish surgical clip crimping about tissue and, thereafter, severing or transecting tissue.

18 Claims, 4 Drawing Sheets

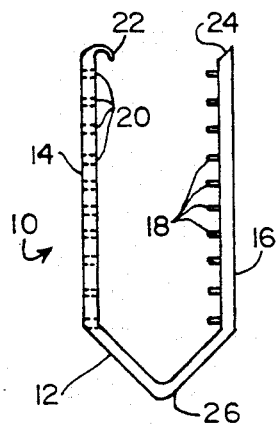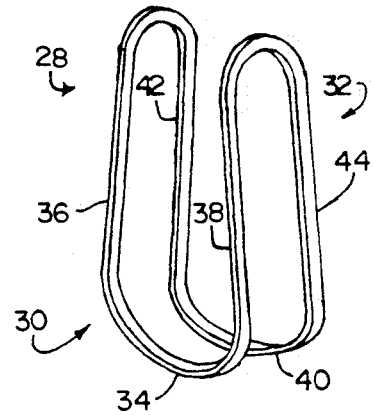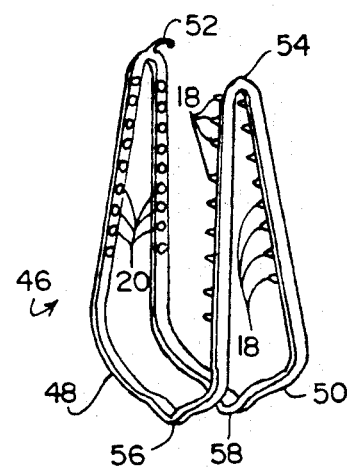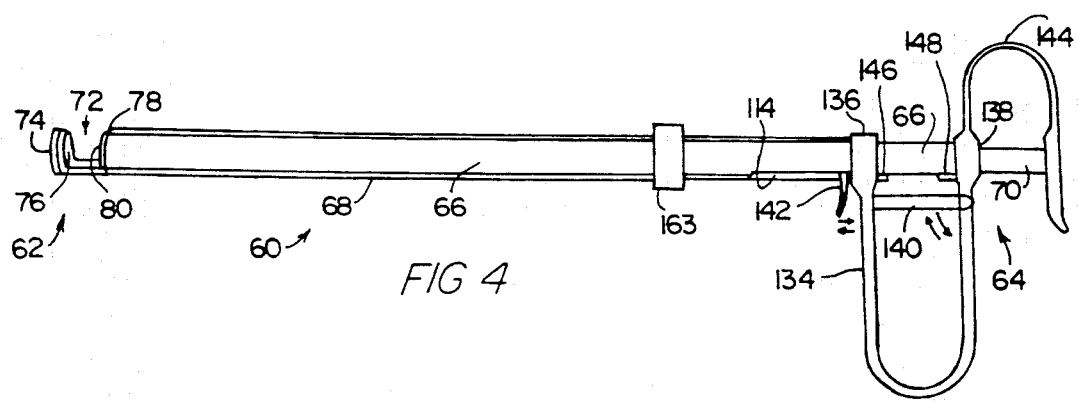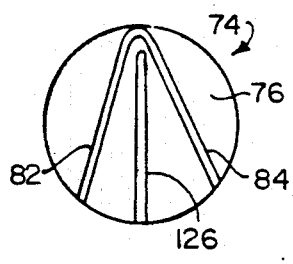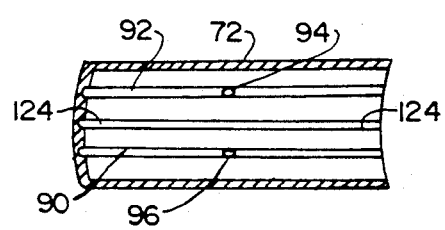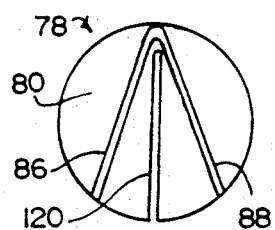

SURGICAL CLIPS AND SURGICAL CLIP APPLICATOR AND CUTTING AND TRANSECTION DEVICE

This application is a continuation of application Ser. No. 07/049,526 filed May 14, 1987 and now abandoned.

BACKGROUND OF THE INVENTION

This invention relates generally to surgical devices and, more particularly, to improved surgical clip structures and an applicator device for applying the surgical clip structure to anatomical tissue. The applicator may also be employed to sever tissue and for transectioning. The improved clip is a single or double U-shaped surgical clip having leg faces with mating projections and apertures for securely locking tissue therebetween. The clips may also include a self-locking feature. The applicator device of the invention includes multiple, telescopically interfitted members for effecting placement of a surgical clip around tissue and crimping thereof, followed by either severing of the crimped tissue or transectioning of the tissue. The applicator includes a cradle for temporarily receiving a surgical clip and facing elements having grooved faces for temporarily restraining or receiving the surgical clip.

There are several prior art patents disclosing somewhat related clips and applicators. For example, U.S. Pat. No. 3,608,544 issued to John W. Schnepper is directed to an instrument for applying a pair of hemostatic clips to a tubular body member to clamp it and then to cut off a portion of the body member between the clips, and, thereafter, positioning or placing the cut off portion in a pocket in the instrument for subsequent use as a biopsy specimen.

U.S. Pat. No. 3,665,924 assigned to Douglas G. Noiles et al concerns an instrument for suturing a tubular body member with a pair of spaced surgical staples and thereafter dividing the body member at a position intermediate the staples.

U.S. Pat. No. 4,349,028 issued to David T. Green shows a ligating and dividing apparatus in which the motion sequence includes clamping tissue, crimping surgical staples around the tissue, and cutting through the ligated tissue between the staples. The apparatus includes semi-automatic and interrupt features unrelated to the present invention. A similar instrument is disclosed in U.S. Pat. No. 4,556,058, also issued to David T. Green, the instrument including spaced apart channels containing surgical ligatures of plastic material and a cutting mechanism intermediate the two channels for dividing the tissue after ligation.

Another, similar structure is seen in U.S. Pat. No. 4,569,346 issued to James W. Poirier. The apparatus includes structure for ligating tissue and dividing the tissue between ligatures and a safety mechanism preventing tissue from being severed if two clips are not properly positioned for securement to the tissue. Another similar apparatus having a safety feature is disclosed in U.S. Pat. No. 4,576,165 issued to David T. Green et al.

None of these prior art patents discloses the surgical clip of this invention which may be a single or double clip and having a cooperating pin projections and apertures for more securely locking tissue. Furthermore, this prior art fails to disclose an instrument for accomplishing placement of the clip followed by severing or transectioning of tissue by a rather uncomplicated applicator and tissue severing device.

SUMMARY OF THE INVENTION

Accordingly, it is a principal object of this invention to provide a novel surgical clip in the form of a U-shaped element having legs with surfaces including mating pin projections and apertures, the element being clipped around anatomical tissue.

It is another object of the invention to provide a surgical clip in the form of an integral, one-piece, generally double U-shaped structure for crimping tissue at two locations, simultaneously.

It is a further object of the invention to provide an improved surgical clip including self-locking members which become interengaged during crimping of the clip in place.

It is yet another object of the invention to provide an improved surgical clip applicator including multiple, telescopically interfitted members for placing a clip around tissue, engaging the same, and then dividing the tissue, centrally within the applicator.

Yet a further object of the invention is to provide an improved surgical clip applicator which is uncomplicated in structure and function and thus low in cost of manufacture.

BRIEF DESCRIPTION OF THE DRAWINGS

Further and more complete objects and advantages of the invention will become readily apparent by reference to the following detailed specification and drawings in which:

FIG. 1 is an elevation, perspective view of one embodiment of a novel surgical clip of this invention;

FIG. 2 is a view similar to FIG. 1 but showing a double U-shaped surgical clip of this invention;

FIG. 3 is a view similar to FIG. 2 but showing another embodiment of the surgical clip of this invention;

FIG. 4 is an elevation, largely diagramatic view showing one embodiment of the applicator device of this invention;

FIG. 5 is a detailed, enlarged scale elevation view showing a portion of the temporary clip retaining structure of the applicator of this invention;

FIG. 6 is a detailed, enlarged scale plan view of the applicator cradle which temporarily receives the surgical clip;

FIG. 7 is a view similar to FIG. 5;

DESCRIPTION OF THE PREFERRED EMBODIMENTS

Figure 8:
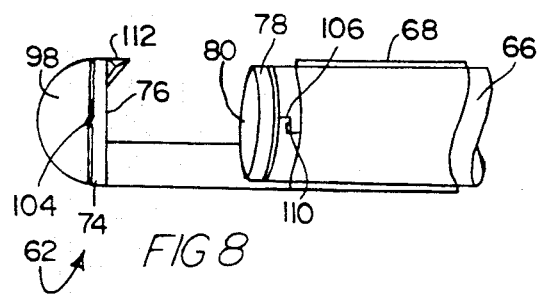
FIG. 8 is an enlarged scale detail view taken from the extreme left-hand portion of FIG. 4.

Referring now to the drawings by reference character and, in particular, to FIG. 1 thereof, an embodiment of the surgical clip 10 is shown which is in the form of a generally U-shaped element. Clip 10 includes a base 12 and a pair of upstanding legs 14, 16. The base 12 may be V-shaped as illustrated or in the form of a gentle curve or semicircle (not shown). The leg 16 is provided with a series of pin projections 18 therealong which face leg 14. Leg 14 includes a series of apertures 20 arranged therealong, adapted to the matingly fit with apertures 18 when the surgical clip is crimped about tissue. The top ends of legs 14 and 16 are provided with interlocking structure such as a hook 22 and angled end 24; when the clip is crimped, hook 22 will slip over and firmly engage end 24, thus further assuring secure locking of clip 10 in place about tissue.

As is clear from FIG. 1, each leg 14, 16 is formed generally as a flat, ribbon-like element. The V-shaped base is so formed as to provide a downwardly directed, applicator device engaging projection 26. This feature will be explained further in detail below.

With reference to FIG. 2, a surgical clip 28 is shown which is an integral, one-piece clip made up of generally double U-shaped elements 30, 32. Element 30 includes a first base 34 and a first pair of upstanding legs 36, 38. U-shaped element 32 includes a second base 40 and a second pair of upstanding legs 42, 44. The upper ends of legs 36, 42 and 38, 44 are integrally joined together. Thus, when clip 28 is crimped around tissue, legs 36, 38 provide one ligature and legs 42, 44 provide a second ligature, respectively. Referring now to FIG. 3, another embodiment of a surgical clip 46 of this invention is illustrated. Clip 46 is another integral, one-piece generally double U-shaped structure with U-shaped elements 48, 50, similar to those shown in FIG. 2. Further, the legs of these elements are provided with pin projections 18 and apertures 20, per the embodiment of the invention illustrated in FIG. 1. Also similar to the embodiment of FIG. 1, a snap hook 52 may be provided which engages the opposite side of the clip at 54 when the clip is crimped together about tissue. The bases of clip 46 may be provided with a downwardly directed, applicator tool engaging projections 56, 58 which are similar to the projection 26 of clip 10 (FIG. 1). Again, details of these tool engaging projections will be explained below.

The clips 10, 28 and 46 may be formed of any suitable non-tissue reactive, medical grade implantable material.

Referring now to FIGS. 4–7, a first embodiment of an applicator device 60 of the invention will be discussed. Applicator device 60 includes multiple, telescopically interfitted, slidable members and the applicator device 60 has a distal end 62 and a proximal end 64. The basic components of applicator device 60 include a first, inner, elongate cylindrical member 66 which is telescopically received within an outer, elongate tubular member 68. There is an additional, inner elongate cylindrical member 70 which has structure and function which will be explained in detail herein below.

The distal end of outer tubular member 68 is formed as an upwardly open, surgical clip receiving cradle 72. The distal end of cradle 72 is closed by a generally vertically oriented surgical clip engaging wall 74 having a proximally facing, clip engaging, grooved surface 76. Similarly the extreme distal end of inner member 66 is provided with a wall 78 provided with a grooved, surgical clip receiving surface 80 which faces distally of the device.

FIG. 5 illustrates one embodiment of surface 76, FIG. 6 illustrates one embodiment of cradle 72, and FIG. 7 illustrates one embodiment of surface 80. Surface 76 is grooved as at 82, 84 to receive, for example, legs 36, 42, respectively, of clip 30 (FIG. 2). Similarly, surface 80 is grooved at 86, 88, to receive legs 38, 44, respectively, of clip 30. The clip 46 (FIG. 3) may be placed in the applicator device 60 in the same manner, with the apertured legs contacting one of the surfaces 76, 80 and the pin projection legs received within grooves of the other surface. As for the FIG. 1 embodiment, two clips 10 would be placed in applicator device 60, with legs 14, 16 of each clip 10 lying in an imaginary plane parallel the long axis of applicator 60.

With reference to FIG. 6, the interior of cradle 72 is provided with a pair of outboard, longitudinal grooves 90, 92 which are dimensioned and arranged to received bases 34, 40 of clip 30, bases 48, 50 of clip 46, or two bases 12 of clip 10. Clip base projection receiving apertures 94, 96 are located centrally of cradle 72 which engage either projections 56, 58 of clip 46 or two projections 26 of two bases 12 of two clips 10. Thusly, a surgical clip assembly or structure may be snugly and securely although temporarily received within cradle 72 and nestled between grooved surfaces 76 and 80.

Figure 9:
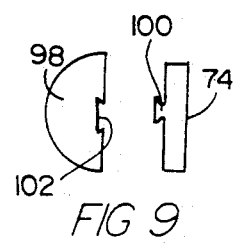
FIGS. 9 and 10 are detailed views of components of the applicator as shown in FIG. 8.
Figure 10:
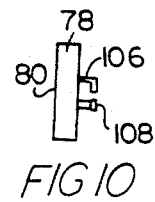
Figure 11A:
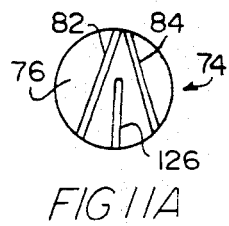
Figures 11A and 11B are views similar to FIGS. 5 and 7, respectively, but showing another embodiment of clip retaining structure.
Figure 11B:
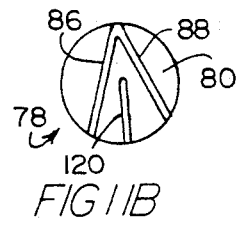
Figure 12A:
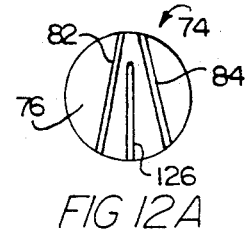
FIGS. 12A, 12B; 13A, 13B; and 14A, 14B are views similar to FIGS. 11A and 11B but showing other embodiments of the invention.
Figure 12B:
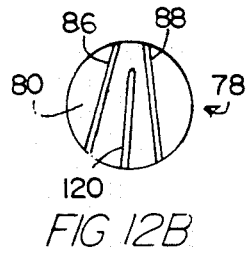
Figure 13A:
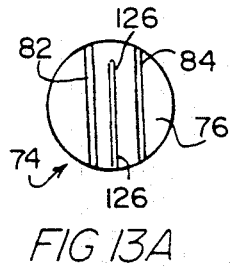
Figure 13B:
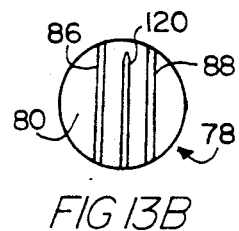

Referring now to FIGS. 11A–14B, the surfaces 76, 80 may be grooved in a wide variety of patterns depending on the type and structure of surgical clip selected. Of course, the surgical clip selected could be an otherwise conventional staple or clip or, rather, pairs of clips. In order to accomplish multiple selection of surfaces without need of providing multiple applicators, the walls 74 and 78 may be removably mounted, as illustrated in FIGS. 8-10. FIG. 9 is a top plan view taken from the extreme distal portion of FIG. 8. The extreme distal end of cradle 72 is formed as an upstanding mounting end 98 for a wall 74. Wall 74 is mounted in end 98 by, for example, a tongue and dovetail groove arrangement illustrated at 100 102. To assure securement of wall 74 in end 98, a cooperating detent and recess structure may be provided, one of which is illustrated at 104.

Another removable mounting arrangement is illustrated in FIG. 10. In this case, the proximally facing side of wall 78 includes a pair of bayonet projections 106, 108 received in mating slots on the distal end of inner member 66, and one of these slots is illustrated at 110 in FIG. 8. Alternatively, of course, both walls may be mounted employing the structure of FIG. 9 or both walls could be removably mounted by employing the structure illustrated in FIGS. 10 and 8.

As shown in FIG. 8, the upper end of a wall 74 can be provided with a proximally directed, tissue engaging projection 112 which facilitates the placing of tissue within cradle 72, embraced by a surgical clip.

Figure 14A:
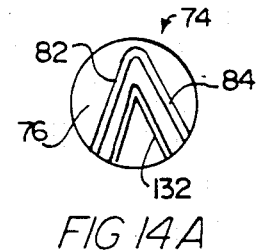
Figure 14B:
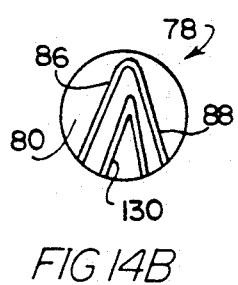
Figure 15:
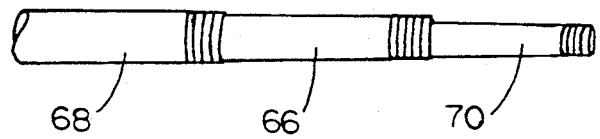
FIG. 15 is a perspective view with parts removed to reveal interior details of the applicator structure.
Figure 16:
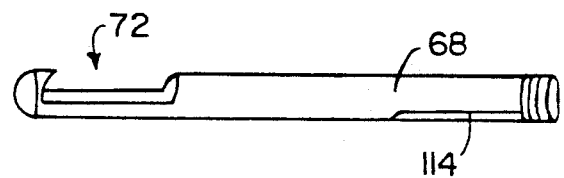
FIGS. 16 and 17 are elevation views of portions of the applicator device shown in FIG. 15.
Figure 17:
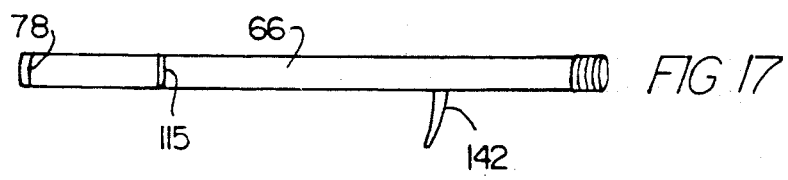
Figure 18:
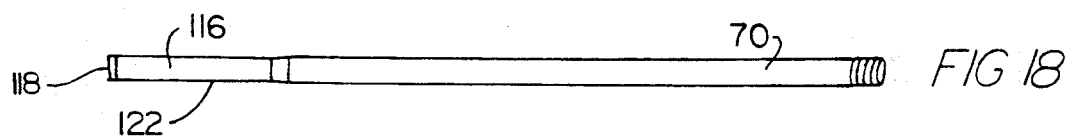
FIG. 18 is an elevation view of one embodiment of a cutting blade and mounting therefore.
Figure 19:
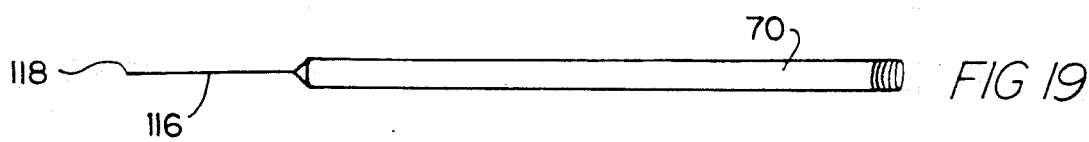
FIG. 19 is a top plan view of the structure shown in FIG. 18.
Figure 20:
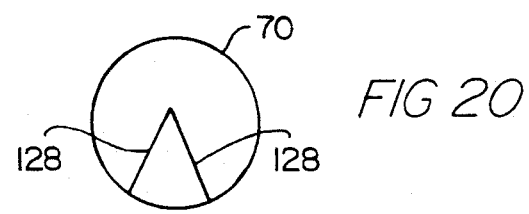
FIG. 20 is an enlarged scale, front view of a cutting blade used for transectioning.

Internal structural details of the applicator device will become apparent by reference to FIGS. 4 and 15-20. As shown in FIG. 15, additional inner member 70 is telescopically, slidably received within inner member 66 which, in turn, is telescopically, slidably received in outer member 68. As seen in FIG. 16, the proximal, lower end of outer member 68 includes a slot 114 formed therethrough for a reason to be discussed below. Inner member 66 has an interior partition at 115. Referring to FIG. 18, the distal end of additional inner member 70 has a cutting member 116 mounted thereon equipped with a cutting blade edge 118 at the distal end thereof. Additional inner member 70 is slidably mounted within inner member 66 so that the cutting blade 116 projects through a slot formed in partition 115 and also extends through a generally vertically oriented slot 120 formed through wall 78, as is more clearly shown in FIG. 7. The lower edge 122 of blade 116 is guided during travel by a blade receiving guide 124 formed centrally, internally within cradle 72 as is best illustrated in FIG. 6. A distal travel of blade 116 is arrested or limited by an abutment stop groove 126 formed in surface 76 of wall 74, as is best seen in FIG. 5. As can be seen in FIGS. 20 and 14A, 14B, the blade 116 might take the form of an inverse, V-shaped blade 128 when it is desired to perform a transection. Thus, with reference to FIG. 14B, wall 78 has an inverse, V-shaped slot 130 formed therethrough and wall 74 has an inverse, V-shaped abutment stop 132 formed in surface 76. If desired, the interior of cradle 72 may be provided with a pair of longitudinal grooves for receiving and guiding the lower edges of inverse, V-shaped blade 128 (not shown).

Referring now to the proximal end of applicator 60 and as shown in FIG. 4, a first, squeezable, U-shaped handle is illustrated at 134. The distal end of the handle 134 is secured to the proximal end of outer member 68 at 136 and the proximal end of handle 134 is secured to the proximal end of inner member 66 as is shown at 138. Thus, when a squeezing action is exerted on handle 134, inner member 66 is caused to move distally with respect to outer member 68, thus to crimp a surgical clip about tissue located within cradle 72. A pivoting lock member 140 is provided with handle 134 to temporarily disable or prevent the squeezing action on handle 134 just described. The reason for lock 140 will be discussed below.

Handle 134 may be of integral, one-piece construction as illustrated in FIG. 4 and could be made of a material such as spring steel. Alternatively, handle 134 might be bifurcated centrally into two handle portions, spring urged apart at the point of bifurcation (not shown). A finger grip 142 depends from inner member 66 and extends through the slot 114 of outer member 68. When finger grip 142 is moved proximally with respect to the distal portion of handle 134, inner member 66 and wall 78 are moved in a proximal direction, thus to open cradle 72 and allow insertion of a surgical clip therewithin. Release of finger grip 142 then causes a surgical clip to be engaged between walls 74 and 78 due to the spring return action of handle 134. An additional, inverse U-shaped handle 144 interconnects the proximal end of inner member 66 with the proximal end of additional inner member 70. A squeezing action exerted on handle 144 thus causes inner member 70 to move in a distal direction with respect to both inner member 66 and outer member 68 to advance blade 116 and its cutting edge 118 thus to effect a tissue severing action.

The procedure would be a transection if blade 116 were replaced by the inverse V-shaped blade 128 of FIG. 20.

A discussion of the operation of the invention now follows. A surgical clip is placed in cradle 72 in the manner just described. During this step, pivoting lock 140 is in the horizontal disposition shown in order to prevent a squeezing action on handle 134 as finger grip 142 is moved in a proximal direction. Thereafter, applicator 60 is manipulated so as to place anatomical tissue within cradle 72. Thereafter, pivoting lock 140 is swung downwardly, to a non-locking position. Then, handle 134 is squeezed so as to ligate anatomical tissue within cradle 72 at two locations along lines formed by, for example, grooves 82 and 84 (see FIG. 5). Thereafter, one of two procedures can be followed. In the first, handle 134 is released and the pivoting lock 140 is pivoted back to its locking position. Then, handle 144 is squeezed in order to move either cutting blade 116 or transection blade 128 distally along cradle 72 to wall 74 and thus either sever or transection tissue located within cradle 72.

An alternative method is as follows. A temporary, interlock structure 146, 148 may be provided on handle 134 as is illustrated in FIG. 4. Handle 134 is squeezed until members 146 and 148 interlock. This also assures that wall 78 has traveled a sufficient distance to assure a secure engagement of a surgical clip around anatomical tissue. Thereafter, handle 144 may be squeezed to effect either a tissue severing or a tissue transectioning procedure. Then, interlocks 146, 148 are released whereupon handles 134 and 144 return to their initial positions as illustrated in FIG. 4.

Figure 21:
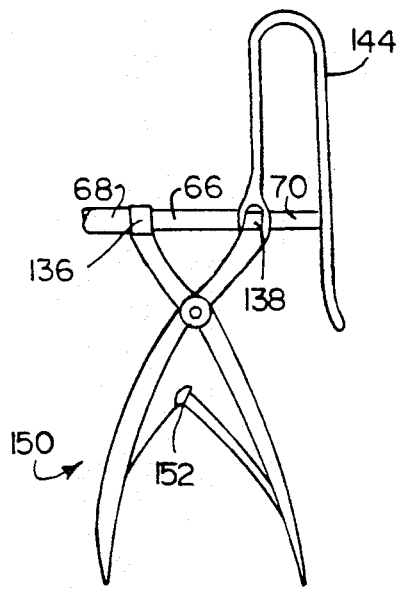
FIG. 21 is a view similar to and taken from the right-hand portion of FIG. 4 but showing another embodiment of handle means for operating the applicator device.

A different form of handle 134 is shown in FIG. 21. The figure discloses a pliers type handle 150 spring urged apart at 152. Otherwise, the structure and function of handle 150 is the same as the structure and function of handle 134.

Figure 22:
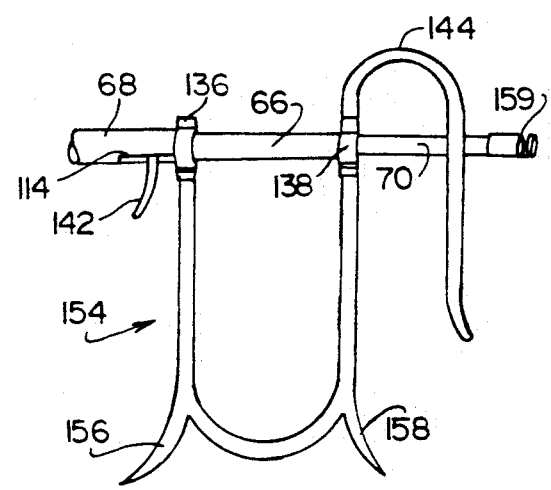
FIG. 22 is a view similar to FIG. 21 but showing yet another embodiment of the invention.

Yet another embodiment of a handle 154 replacing handle 134 is illustrated in FIG. 22. Handle 154 is structured to function in exactly the same manner as handle 134. For the sake of comfort, however, curved projections 156 and 158 are provided to provide a more comfortable hand grip for the user. Also, the proximal end of additional inner member 70 may be extended and fitted with an otherwise conventional electrical connector 159.

Figure 23:
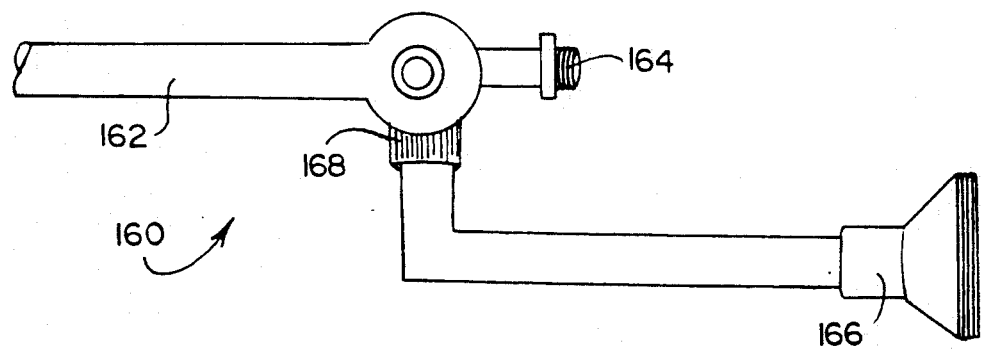
FIG. 23 is a top plan view of a laparoscope or endoscope with which the applicator device of this invention may be employed and inserted therethrough.

Of course, the applicator device 60 will be used with either a conventional laparoscope or endoscope or one as shown in FIG. 23 and identified at 160. Laparoscope 160 includes an elongate, opened tubular portion 162 into which device 160 is inserted and secured therein as by a knurled, internally threaded nut 163 (FIG. 4) threaded onto threaded, proximal end 164 of laparoscope 160. Laparoscope 160 includes an eye piece assembly 166 pivotally mounted to tube 160 at 168 so as to be adjustable and greatly facilitate its use by the surgeon.

The invention may be embodied in other specific forms without departing from the spirit or central characteristics thereof. The present embodiments are therefore to be considered in all respects as illustrative and not restrictive, the scope of the invention being indicated by the appended claims rather than by the foregoing description and all changes which come from within the meaning and range of equivalency of the claims are therefore intended to be embraced therein.

I claim:

1. A surgical clip and an applicator device for use in applying said surgical clip to anatomical tissue, said applicator device comprising an inner elongate member slidably telescopically received within an outer tubular member, said inner and outer members each having a distal end and a proximal end, the distal end of said outer member defining an upwardly opened, surgical clip receiving cradle having a distal end and a proximal end, a first upstanding, proximally directed, surgical clip engaging wall means on said cradle distal end, said cradle proximal end formed in part by a portion of said outer member and in part by a second, distally directed, surgical clip engaging wall means on said inner elongate member distal end, said second clip engaging wall means being slidably received within said portion of said outer member forming said cradle proximal end, each of said wall means having a surface thereon grooved to temporarily receive a portion of said surgical clip therewithin, said surgical clip comprising an integral unitary generally double U-shaped member including a first generally U-shaped element having a fist base and a pair of first upstanding legs extending from said first base and terminating in first upper ends and a second generally U-shaped element having a second base and a pair of second upstanding legs extending from said second base and terminating in second upper ends, said first upper ends being integrally joined to said second upper ends to form a first joined pair of legs including a first leg and a second leg and a second joined pair of legs including a first leg and a second leg, said first and second legs being dimensioned and configured to receive and clamp anatomical tissue therebetween when crimped, said surgical clip being received in said clip receiving cradle such that the first and second legs of one joined pair of said upstanding legs are received within the grooves on one of said clip engaging wall means, and the first and second legs of the other joined pair of said upstanding legs are received within the grooves on the other of said clip engaging wall means, said applicator being manipulable whereby anatomical tissue is placed within said cradle, said applicator further including means to slide said inner member within said outer member in a distal direction with respect to said outer member, whereby said second clip engaging wall means moves toward said first clip engaging wall means to crimp said surgical clip about the tissue, said surgical clip being crimped by said second clip engaging wall means causing the first leg of said joined pair of legs received within said grooves in said second clip engaging wall means to be brought toward the first leg of the other of said joined pair of legs and the second leg of said joined pair of legs received within said grooves in said second clip engaging wall means to be brought toward the second leg of the other of said joined pair of legs.

2. The surgical clip and applicator device as claimed in claim 1 wherein said first wall means is detachably mounted on said cradle distal end and said second wall means is detachably mounted on said inner elongate member distal end.

3. The surgical clip and applicator device as claimed in claim 1 wherein the interior of said cradle further comprises surgical clip temporary mounting means therein.

4. The surgical clip and applicator device as claimed in claim 1 wherein said proximally directed wall means further comprises a proximally directed, tissue engaging projection formed on the upper end of said proximally directed wall means.

5. The surgical clip and applicator device as claimed in claim 1 further comprising a second inner member slidably telescopically received within said inner elongate member, said second inner member having a proximal end and a distal end, said second inner member distal end having distally directed cutting blade means thereon, said second wall means on said inner member distal end including a slot therethrough adapted to matingly slidably engage said cutting blade means, and means for moving said second inner member in a distal direction separate from said sliding movement of said inner elongate member, whereby in use and after placement of tissue in said cradle, said second inner member may be selectively moved within said inner elongate member in a distal direction with respect to both said inner and outer members to sever the tissue.

6. The surgical clip and applicator device as claimed in claim 5 wherein said cutting blade means comprise a generally vertically oriented, single cutting blade.

7. The surgical clip and applicator device as claimed in claim 6 wherein said proximally directed wall means surface further includes a grooved abutment stop for defining the distal limit of travel of said cutting blade.

8. The surgical clip and applicator device as claimed in claim 5 wherein said cutting blade means comprise, in cross-section, a generally inverse, V-shaped cutting blade assembly.

9. The surgical clip and applicator device as claimed in claim 8 wherein said proximally directed wall means surface further includes a generally inverse, V-shaped grooved abutment to for defining the distal limit of travel of said inverse V-shaped cutting blade assembly, and said slot means of said distally directed wall means is a generally inverse, V-shaped slot for receiving said V-shaped cutting blade assembly.

10. The surgical clip and applicator device as claimed in claim 5 further comprising additional U-shaped handle means joining said second inner member proximal end and said inner member proximal end whereupon a squeezing action exerted on said additional handle means causes said additional inner manner to move distally with respect to said inner member.

11. The surgical clip and applicator device as claimed in claim 1 further comprising U-shaped handle means joining said outer member proximal end and said inner member proximal end whereupon a squeezing action exerted on said handle means causes said inner member to move distally with respect to said outer member.

12. The surgical clip and applicator device as recited in claim 11, further comprising temporary, displaceable locking means preventing squeezing action operation of said handle means.

13. The surgical clip and applicator device as recited in claim 11 further comprising means for temporarily interengaging portions of said handle means after a squeezing action has been exerted on said handle means.

14. The surgical clip and applicator device as claimed in claim 10 further comprising means for moving said inner member proximally with respect to said outer member including means defining an elongate slot through a proximal portion of said outer member and a finger grip mounted on said inner member and extended through said outer member elongate slot means.

15. The surgical clip and applicator device as claimed in claim 1 further comprising pliers configured handle means joining said outer member proximal end and said inner member proximal end whereupon a squeezing action exerted on said pliers configured handle means causes said inner member to move distally with respect to said outer member, and means for biasing said pliers configured handle means to an open position.

16. The surgical clip and applicator device as claimed in claim 1 wherein each of the legs of one joined pair is provided with a series of pin projections therealong and facing the other joined pair of legs, each of the legs of said outer joined pair of legs is provided with a series of apertures therealong arranged for mating fit with said pin projections whereby, when said clip is crimped about tissue, said pin projections are caused to pass through the tissue and enter said apertures.

17. The surgical clip and applicator device as claimed in claim 1 wherein said cradle interior includes means defining a pair of elongate grooves therein for receiving the respective bases of said surgical clip assembly.

18. The surgical clip and applicator device as claimed in claim 17 wherein each said base further includes a downwardly directed applicator tool engaging projection, the grooves of said cradle further including means defined therein for receiving said base projections.

* * * * *